US00PP16428P2

(12) United States Plant Patent
Verschoor

(10) Patent No.: US PP16,428 P2
(45) Date of Patent: Apr. 11, 2006

(54) ***VERONICA* PLANT NAMED 'BABY DOLL'**

(50) Latin Name: *Veronica hybrida*
Varietal Denomination: Baby Doll

(75) Inventor: Jan Verschoor, Haarlem (NL)

(73) Assignee: Witteman & Co., Hillegom (NL)

( * ) Notice: Subject to any disclaimer, the term of this patent is extended or adjusted under 35 U.S.C. 154(b) by 78 days.

(21) Appl. No.: 11/073,469

(22) Filed: Mar. 5, 2005

(51) Int. Cl.
*A01H 5/00* (2006.01)

(52) U.S. Cl. ..... Plt./251

(58) Field of Classification Search ..... Plt./251
See application file for complete search history.

*Primary Examiner*—Anne Marie Grunberg
(74) *Attorney, Agent, or Firm*—C. A. Whealy

(57) ABSTRACT

A new and distinct cultivar of *Veronica* plant named 'Baby Doll', characterized by its upright, compact and sturdy plant habit; freely basal branching habit; dense and bushy plant form; long flower racemes; freely flowering habit; and light red purple-colored flowers.

2 Drawing Sheets

Botanical designation: *Veronica hybrida.*
Cultivar denomination: 'Baby Doll'.

BACKGROUND OF THE INVENTION

The present Invention relates to a new and distinct cultivar of *Veronica* plant, botanically known as *Veronica hybrida,* and hereinafter referred to by the cultivar name 'Baby Doll'.

The new *Veronica* is a product of a planned breeding program conducted by the Inventor in Haarlem, The Netherlands. The objective of the breeding program was to create sturdy new *Veronica* cultivars with numerous flowers with attractive coloration.

The new *Veronica* originated from a cross-pollination made by the Inventor in July, 1998 of a proprietary *Veronica longifolia*×*Veronica spicata* selection, not patented, as the female, or seed, parent with a proprietary *Veronica spicata*× *Veronica longifolia* selection, not patented, as the male, or pollen, parent. The new *Veronica* was discovered and selected by the Inventor during the summer of 2000 as a single flowering plant within the progeny of the stated cross-pollination in a controlled environment in Haarlem, The Netherlands.

Asexual reproduction of the new cultivar by cuttings since 2001 in Haarlem, The Netherlands, has shown that the unique features of this new *Veronica* are stable and reproduced true to type in successive generations.

SUMMARY OF THE INVENTION

Plants of the cultivar Baby Doll have not been observed under all possible environmental conditions. The phenotype may vary somewhat with variations in environment such as temperature and light intensity without, however, any variance in genotype.

The following traits have been repeatedly observed and are determined to be the unique characteristics of 'Baby Doll'. These characteristics in combination distinguish 'Baby Doll' as a new and distinct *Veronica* cultivar:

1. Upright, compact and sturdy plant habit.
2. Freely basal branching habit, dense and bushy plant form.

3. Long flower racemes.
4. Freely flowering habit.
5. Light red purple-colored flowers.

Plants of the new *Veronica* can be compared to the parent selections. Compared to plants of the parent selections, plants of the new *Veronica* are more compact, are sturdier, have shorter flower racemes and have more distinct flower coloration.

Plants of the new *Veronica* can be compared to plants of the *Veronica* cultivar Sunny Border Blue, not patented. Plants of the new *Veronica* differ from plants of the cultivar Sunny Border Blue in the following characteristics:

1. Plants of the new *Veronica* are more compact and sturdier than plants of the cultivar Sunny Border Blue.
2. Plants of the new *Veronica* have longer flower racemes than plants of the cultivar Sunny Border Blue.
3. Plants of the new *Veronica* have light red purple-colored flowers whereas plants of the cultivar Sunny Border Blue have blue violet-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Veronica.*

The photograph on the first sheet comprises a side perspective view of a typical flowering plant of 'Baby Doll' grown in a container.

The photograph at the top of the second sheet is a close-up view of a typical flower raceme of 'Baby Doll'.

The photograph at the bottom of the second sheet is a close-up view of a typical leaf of 'Baby Doll'.

DETAILED BOTANICAL DESCRIPTION

Plants shown in the aforementioned photographs and used in the following description were grown under conditions which closely approximate commercial production conditions during the late spring and summer in an outdoor nursery in Lisse, The Netherlands. During the production of the plants, day temperatures ranged from 10 to 30° C. and night temperatures ranged from 4 to 15° C. Plants were about two years old when the photograph and description were taken. In the following description, color references are made to The Royal Horticultural Society Colour Chart, 2001 Edition, except where general terms of ordinary dictionary significance are used.

Botanical classification: *Veronica hybrida* cultivar Baby Doll.

Parentage:

*Female, or seed, parent.*—Proprietary *Veronica longifolia*×*Veronica spicata* selection, not patented.

*Male, or pollen, parent.*—Proprietary *Veronica spicata*×*Veronica longifolia* selection, not patented.

Propagation:

*Type.*—By cuttings.

*Time to produce a rooted young plant.*—About one month during the spring.

*Root description.*—Thick; freely branching.

Plant description:

*Form.*—Perennial. Upright, compact and sturdy plant habit; narrow inverted triangle. Freely basal branching with about 17 flowering stems per plant; dense and bushy plant habit; moderately vigorous growth habit. Numerous flowers arranged on crowded terminal racemes.

*Plant height.*—About 38 cm.

*Plant width.*—About 33 cm.

*Lateral stem description.*—Length (excluding inflorescence): About 21.3 cm. Diameter: About 3 mm. Internode length: About 4.6 cm. Strength: Strong. Texture: Smooth, glabrous. Color: 144A to 144B.

*Foliage description.*—Arrangement: Opposite, simple. Length: About 7.2 cm. Width: About 2.7 mm. Shape: Lanceolate. Apex: Acute. Base: Attenuate. Margin: Serrate. Texture, upper and lower surfaces: Smooth, glabrous. Venation pattern: Pinnate. Color: Developing foliage, upper surface: 141A to 143A. Developing foliage, lower surface: 137B to 143A. Fully expanded foliage, upper surface: 137A. Fully expanded foliage, lower surface: 137D to 138A. Venation, upper surface: 143C. Venation, lower surface: 144A to 144B. Petiole length: Lower leaves, about 1.7 cm; upper leaves, sessile. Petiole diameter: About 3 mm. Petiole color: 144A.

Flower description:

*Flower arrangement and shape.*—Single campanulate flowers closely spaced on upright terminal racemes; flowers face mostly outward. Freely flowering habit, about 225 flowers per raceme. Natural flowering season: Continuous flowering from July to late September in The Netherlands.

*Flower longevity on the plant.*—Individual flowers last about one week on the plant. Flowers not persistent.

*Flower buds.*—Length: About 5 mm. Diameter: About 2 mm. Shape: Narrowly ovoid. Color: 70C to 73B.

*Inflorescence size.*—Length: About 16.7 cm. Diameter: About 2.4 cm.

*Flowers.*—Diameter: About 5 mm. Depth (height): About 9 mm.

*Petals.*—Arrangement: Campanulate; four petals fused towards the base. Length: About 6 mm. Width: About 2.5 mm. Shape: Oblanceolate. Apex: Broadly acute. Margin: Entire. Texture: Smooth, glabrous. Color: When opening, upper surface: 68B. When opening, lower surface: 68A. Fully opened, upper and lower surfaces: 68A.

*Sepals.*—Arrangement: Four sepals fused towards the base; lower two sepals twice as long as upper two sepals. Length: Upper sepals: About 3 mm. Lower sepals: About 6 mm. Width: Upper sepals: About 1 mm. Lower sepals: About 1.5 mm. Shape: Ovate. Apex: Acute. Base: Fused. Margin: Entire. Texture, upper and lower surfaces: Smooth, glabrous. Color, upper and lower surfaces: 137B.

*Peduncles.*—Length: About 16.7 cm. Diameter: About 3 mm. Aspect: Erect to 30° from vertical. Strength: Strong. Color: 143A.

*Pedicels.*—Length: About 1 mm. Diameter: About 0.5 mm. Aspect: About 55° from vertical. Strength: Strong. Color: 143B.

*Reproductive organs.*—Stamens: Quantity per flower: Two. Filament length: About 7 mm. Filament color: 69D. Anther shape: Elliptic. Anther length: About 2 mm. Anther color: 71A to 72A. Pollen amount: Abundant. Pollen color: 2C to 2D. Pistils: Quantity per flower: One. Pistil length: About 8 mm. Stigma shape: Clavate, flattened. Stigma color: 70B. Style length: About 7.5 mm. Style color: 75A to 75B. Ovary color: 143C. Fruit: Length: About 3 mm. Diameter: About 3 mm. Texture: Smooth. Color: 144A to 144B. Seed: Quantity per fruit: About 12. Length: About 1 mm. Diameter: About 1 mm. Texture: Smooth. Color: N199C to N199D.

Disease/pest resistance: Plants of the new *Veronica* have not been noted to be resistant to pathogens and pests common to *Veronica*.

High temperature tolerance: Plants of the new *Veronica* have been observed to tolerate temperatures up to 30° C.

Hardiness: Plants of the new *Veronica* have been observed to be hardy to USDA Zone 4.

It is claimed:

1. A new and distinct cultivar of *Veronica* plant named 'Baby Doll', as illustrated and described.

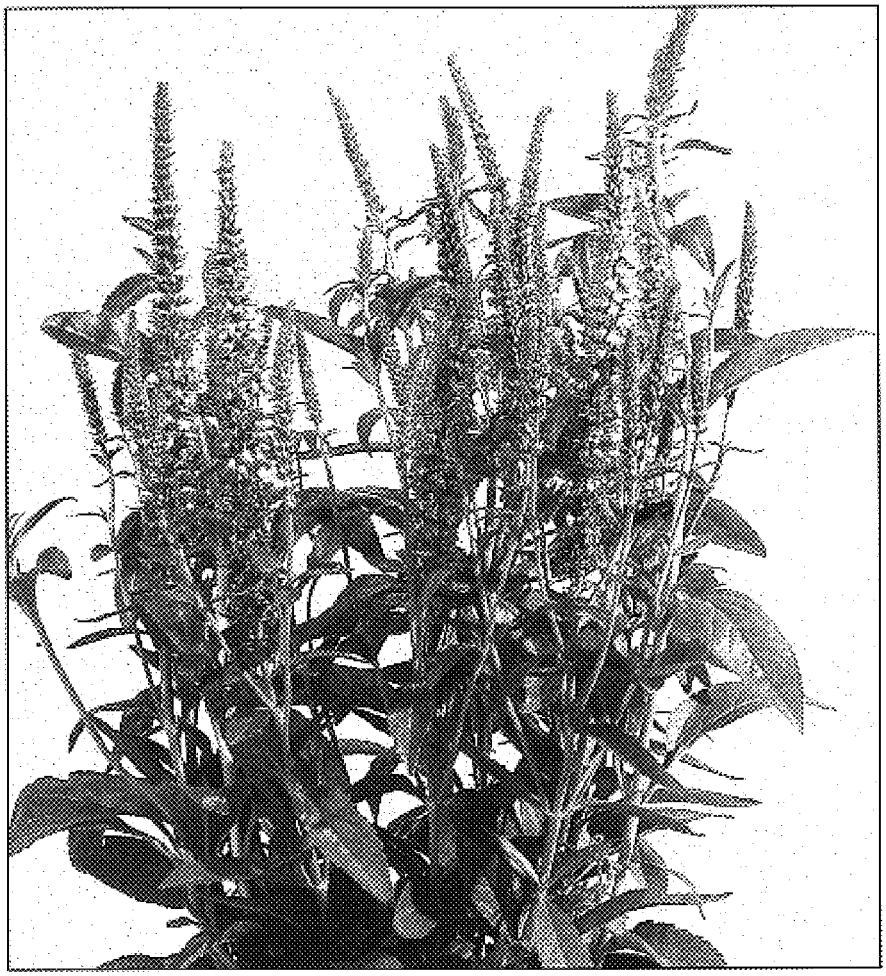

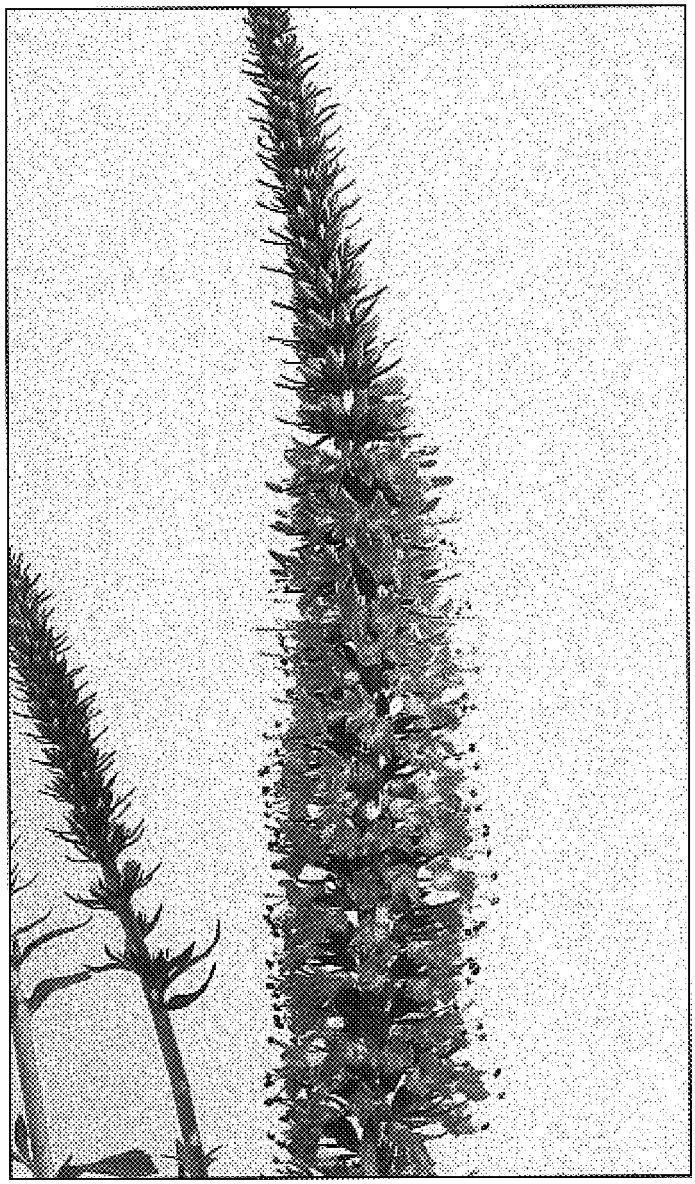
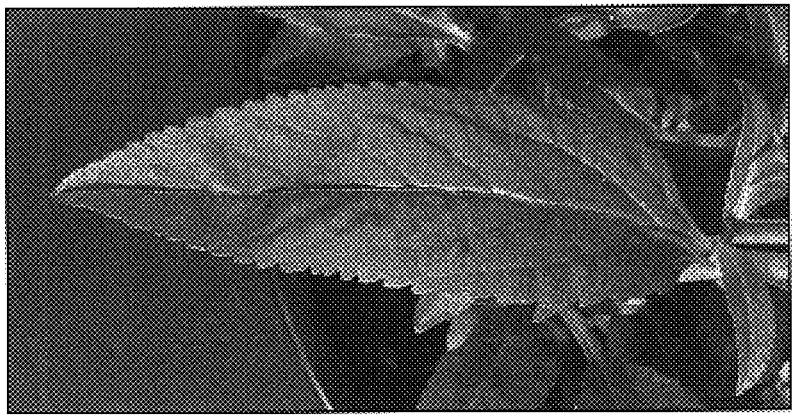

* * * * *